(12) United States Patent
Hofmann

(10) Patent No.: US 6,361,762 B1
(45) Date of Patent: Mar. 26, 2002

(54) PREBRUSHING LIQUID ORAL COMPOSITION

(75) Inventor: William H. Hofmann, St. Louis, MO (US)

(73) Assignee: Vi-Jon Laboratories, Inc., St. Louis, MO (US)

( * ) Notice: Subject to any disclaimer, the term of this patent is extended or adjusted under 35 U.S.C. 154(b) by 0 days.

(21) Appl. No.: 09/862,135

(22) Filed: May 21, 2001

(51) Int. Cl.⁷ .............................. A61K 7/16; A61K 7/18
(52) U.S. Cl. .............................. 424/52; 424/49; 424/57
(58) Field of Search .............................. 424/49, 52, 57

(56) References Cited

U.S. PATENT DOCUMENTS

| | | | |
|---|---|---|---|
| 2,054,742 A | | 9/1936 | Elbel |
| 3,004,897 A | | 10/1961 | Shore |
| 3,427,380 A | | 2/1969 | Kirkland |
| 3,864,472 A | | 2/1975 | Pensak et al. |
| 4,081,526 A | | 3/1978 | Asakawa et al. |
| 4,150,151 A | | 4/1979 | Pader et al. |
| 4,152,418 A | | 5/1979 | Pader |
| 4,323,551 A | * | 4/1982 | Parran .................. 424/54 |
| 4,362,639 A | | 12/1982 | Eoga |
| 4,657,758 A | * | 4/1987 | Goldemberg et al. ......... 424/49 |
| 4,666,708 A | * | 5/1987 | Goldemberg et al. ......... 424/49 |
| 4,772,461 A | * | 9/1988 | Parran et al. .................. 424/52 |
| 4,802,841 A | | 2/1989 | Komura et al. |
| 4,822,599 A | | 4/1989 | Mitra |
| 4,853,213 A | | 8/1989 | Thame |
| 4,885,155 A | | 12/1989 | Parran, Jr. et al. |
| 4,913,895 A | | 4/1990 | Miyake et al. |
| 4,925,655 A | | 5/1990 | Smigel et al. |
| 4,950,479 A | | 8/1990 | Hill et al. |
| 4,952,392 A | | 8/1990 | Thame |
| 4,978,521 A | | 12/1990 | Blue |
| 4,980,153 A | * | 12/1990 | Jackson et al. ................. 424/52 |
| 4,994,262 A | | 2/1991 | Charbonneau et al. |
| 4,999,184 A | | 3/1991 | Parran, Jr. et al. |
| 5,015,466 A | | 5/1991 | Parran, Jr. et al. |
| 5,043,183 A | * | 8/1991 | Gershon et al. ............... 424/52 |
| 5,094,844 A | * | 3/1992 | Gaffar et al. .................. 424/52 |
| 5,229,103 A | * | 7/1993 | Eagle et al. ................... 424/49 |
| 5,338,538 A | * | 8/1994 | Tricca et al. .................. 424/57 |
| 5,811,079 A | * | 9/1998 | Yu et al. ....................... 424/52 |

* cited by examiner

Primary Examiner—Shep K. Rose
(74) Attorney, Agent, or Firm—Polster, Lieder, Woodruff & Lucchesi, L.C.

(57) ABSTRACT

A liquid oral composition for loosening and removing accumulated plaque deposits on dental surfaces which has a slightly acidic pH of about 5.0 to less than 7.0 and is stable when stored at 7°–40° C. for prolonged periods. The composition contains 0.15–0.25 wt. % sodium benzoate, 0.025–0.65 wt. % sodium lauryl sulfate and 0.005–0.015 wt. % tetrasodium pyrophosphate as active ingredients.

6 Claims, No Drawings

PREBRUSHING LIQUID ORAL COMPOSITION

CROSS REFERENCE TO RELATED APPLICATIONS

N/A

STATEMENT REGARDING FEDERALLY SPONSORED RESEARCH OR DEVELOPMENT

N/A

BACKGROUND OF THE INVENTION

The invention is concerned with liquid oral prebrushing compositions containing sodium benzoate, sodium lauryl sulfate and small but effective amounts of tetrasodium pyrophosphate. These compositions are designed for removal of plaque from teeth before brushing with a dentifrice. Dental plaque is a problem with the teeth of most persons and consists of a microbial film which adheres firmly to dental surfaces. While it often can be removed with some difficulty by surface cleaning, it has a tendency to reform rapidly so continuous treatment is needed.

Plaque is particularly dangerous when formed on the teeth around the gum surface as it leads to gingivitis, periodontal disease and eventually loss of teeth and jawbone.

While many people can obviate most plaque problems by daily brushing and flossing combined with periodic cleaning by a dental hygienist, for some this is not sufficient. Therefore, it is desirable to have an oral composition which can be used on the teeth prior to brushing to soften and loosen the plaque so that it is more easily removed by the physical abrasion of brushing.

U.S. Pat. No. 5,338,538 uses a combination of pyrophosphate and sodium lauryl sulfate in a prebrushing oral formulation for softening and removal of plaque. The compositions of this patent all have a relatively high concentration of pyrophosphate salt and also operate at an alkaline pH, and tend to have a problem with clouding when stored at cooler temperatures.

BRIEF SUMMARY OF THE INVENTION

The present invention relates to a liquid oral prebrushing composition designed to loosen and remove accumulated plaque deposits, has a slightly acidic pH of about 5.0 to less than 7.0, and contains sodium benzoate, sodium lauryl sulfate and tetrasodium pyrophosphate. The composition remains clear and uniform without any indication of clouding or precipitation when stored in temperatures of 7° C. to 40° C. for prolonged periods.

DETAILED DESCRIPTION OF THE INVENTION

The invention preferably is a clear solution comprising about 6.0 to about 10.0 wt. % ethyl alcohol, about 5.0 to about 15 wt. % of a selected humectant, preferably glycerin or sorbitol, about 0.02 to about 0.075 wt. % sodium lauryl sulfate, about 0.2 to about 0.85 wt. % sodium benzoate, an acid buffer to pH at about 5.5 to about 6.5, sodium saccharin to the desired sweetness level, selected flavors, a soluble thickener which may be added at 0.001 to 0.10 wt. %, and D.&C. or F.D.&C. dyes, as required. Sodium fluoride can be incorporated at a safe and effective level to make the product also a post-brushing rinse. About 0.01 to about 0.05 wt. % tetrasodium pyrophosphate, with the other detergent salts, i.e., sodium benzoate and sodium lauryl sulfate, are effective in loosening and assisting in removing accumulated oral plaque when the product is rinsed over dental surfaces prior to a vigorous brushing.

The most effective manner of combining the foregoing ingredients to provide a clear, stable product is as follows:

1. All alcohol soluble ingredients; namely the solubilizers, benzoic acid, and flavors are added to and mixed into the ethyl alcohol.

2. A separate slurry is prepared by dissolving the sodium lauryl sulfate in a portion of the batch water, adding the soluble gum thickener and mixing until clear.

When clear and uniform, the selected humectant (glycerin or sorbitol solution) can be added and mixed until uniform.

3. The major portion of the purified water is charged into the manufacturing tank, mixing is started and the balance of the water soluble materials are added, namely, sodium benzoate, tetrasodium pyrophosphate, sodium saccharin, dyes, sodium fluoride, if desired, and the balance of the humectant. This is then mixed until uniform. The alcohol phase is next added and mixed. The gum slurry is added and, after mixing until uniform, the batch is completed with purified water, mixed and sampled for specification testing.

The manner of making variations of this dental rinse invention is illustrated by the following examples:

EXAMPLE 1

The following oral rinse composition was formulated:

| A. Alcohol phase, All figures are given as w/w; | |
|---|---|
| Ethyl Alcohol (190 Proof) | 8.675 |
| Flavors | 0.103 |
| Solubilizers | 0.45 |
| Benzoic acid | 0.02 |
| B. Gum slurry; | |
| Water, purified | 5.0 |
| Sodium lauryl sulfate | 0.05 |
| Xanthan gum | 0.005 |
| The Gum slurry is mixed until completely clear, and a glycerin solution is added. If desired, sorbitol can be substituted for glycerin | 1.5–15.0 |
| C. Batch; | |
| Water, purified | 65.0 |
| Glycerin/sorbitol | balance |
| Sodium benzoate | 0.20 |
| Tetrasodium pyrophosphate | 0.01 |
| Sodium saccharin | 0.0035 |
| F.D. & C. dyes | QS |
| Alcohol solution | all |
| Gum slurry | all |
| Water, purified | QS to 100% |
| The result is a clear solution having a pH of 5.5/6.5 | |

The result is a clear solution having a pH of 5.5/6.5

EXAMPLE II

Oral Rinse:

| | % w/w |
|---|---|
| A. Alcohol phase; | |
| Ethyl Alcohol (190 proof) | 6.1814 |
| Flavors | 0.1175 |
| Solubilizers | 0.1500 |
| Benzoic Acid | 0.0190 |

-continued

|  | % w/w |
|---|---|
| B. Water phase: | |
| Water, purified | 85.4559 |
| Humectant | 7.110 |
| Sodium Benzoate | 9.850 |
| Sodium Lauryl Sulfate | 0.050 |
| Tetrasodium Pyrophosphate | 0.050 |
| Soluble gum thickener | 0.0010 |
| Sodium Saccharin | 0.0096 |
| F.D. & C. Dyes | QS |
| C. Batch | |
| The alcohol phase and the water phase are combined and the result is a clear product at a pH of 6.5/6.95 | |

The alcohol phase and the water phase are combined and the result is a clear product at a pH of 6.5/6.95

EXAMPLE III

Pre/post brushing dental rinse:

|  | % wt. |
|---|---|
| Alcohol Phase: | |
| A. Ethyl Alcohol (190 proof) | 6.4837 |
| Flavors | 0.1554 |
| Solubilizer | 0.845 |
| Alcohol solubilized humectant | 7.0253 |
| B. Water phase: | |
| Water, purified | 83.50 |
| Citric Acid | 0.1486 |
| Sodium Benzoate | 0.8450 |
| Sodium Lauryl Sulfate | 0.0498 |
| Sodium Saccharin | 0.0097 |
| Sodium Bicarbonate | 0.4998 |
| Sodium Fluoride | 0.0020 |
| F.D. & C Dyes | QS |
| Water, purified | QS |
| C. Batch | |
| The alcohol phase and the water phase are combined and the resulting product is clear and has a pH of 6.5/6.95 | |

The alcohol phase and the water phase are combined and the resulting product is clear and has a pH of 6.5/6.95

The low level of pyrophosphate, namely about 0.01% $P_2O_7^{-4}$ reduces the cloudiness of the product at lower temperatures, i.e., 10° C.

The combination of sodium benzoate, $P_2O_7^{-4}$ and sodium lauryl sulfate is an effective active ingredient combination which reduces the amount of active ingredients that are needed, and thus tends to eliminate the cloudiness problem in such compositions, particularly when used at a acidic composition of pH about 6.0 to below 7.0. The tetrasodium pyrophosphate is present in an amount of 0.005 to 0.015 wt. %. The sodium lauryl sulfate is present in an amount of about 0.025 to about 0.065 wt. % and sodium benzoate is present in an amount of about 0.15 to about 0.25wt. %. Adding about 0.01% to about 0.05 wt. % benzoic acid produces a buffered pH system in combination with sodium benzoate to produce a finished product having a pH of about 5.5 to about 6.5, and thus a stable product which remains stable on prolonged storage, even at low temperatures The prebrushing composition of the invention may include a humectant to give a moist feel to the mouth. Certain humectants can also impart sweetness to the prebrushing composition. The humectant generally is present in an amount ranging from about 5 to about 25 wt. % of the prebrushing composition. Suitable humectants which may be used include edible polyhydric alcohols, such as sorbitol or glycerol.

The prebrushing composition of the invention may, in addition, include ingredients effective to provide flavoring and coloring. The flavorant may be a flavoring oil, such as, oil of peppermint, spearmint, wintergreen, eucalyptus, lemon, and orange, and sweetening agents such as sucrose, lactose, maltose, saccharine, sodium cyclamate, etc. The amount of flavoring or sweetening agent generally ranges from about 0.002% to about 0.3% of the prebrushing composition.

The prebrushing composition is used in a conventional manner by applying a comfortable amount, such as one tablespoon, in the mouth, and rinsing it about the dental surfaces. A reduction of the amount of plaque on dental surfaces is accomplished when the prebrushing composition of the invention is employed in conjunction with a conventional tooth brushing regimen.

In view of the above, it will be seen that the several objects and advantages of the present invention have been achieved and other advantageous results have been obtained.

As various changes could be made in the above constructions without departing from the scope of the invention, it is intended that all matter contained in the above description or shall be interpreted as illustrative and not in a limiting sense.

Having thus described the invention, what is claimed and desired to be secured by Letters Patent is:

1. A clear, stable prebrushing composition having a slightly acidic pH of about 5.0 to less than 7.0 and comprising as active ingredients sodium benzoate, sodium lauryl sulfate and tetrasodium pyrophosphate.

2. The prebrushing composition of claim 1 that remains clear with no indication of crystal formation, flocculation or sedimentation when stored at temperature conditions of approximately 7° C. to 40° C.

3. The composition of claim 1 having a buffered pH system, comprising a combination 0.15 wt. % to 0.25 wt. % sodium benzoate combined with 0.01 wt. % to 0.05 wt. % benzoic acid to yield a stable finished product pH of 5.5 to 6.5 that remains stable on prolonged storage.

4. The composition of claim 1 containing in percentage by weight to the weight of the completed composition:

a) about 0.15 to about 0.25 wt. % sodium benzoate, b) about 0.025 to about 0.065 wt. % sodium lauryl sulfate, and c) about 0.005 to about 0.015 wt. % tetrasodium pyrophosphate.

5. The composition of claim 1 including a small but effective amount of sodium fluoride and being effective as a post brushing oral rinse.

6. The composition of claim 4 including about 0.002 to about 0.005 wt. % sodium fluoride and said composition is effective as a post brushing oral rinse.

* * * * *